United States Patent [19]

Inoue et al.

[11] Patent Number: 4,910,320

[45] Date of Patent: Mar. 20, 1990

[54] PROCESS FOR PREPARING 3-PYRROLIDINOL

[76] Inventors: Kenji Inoue, 1-13-36-301, Kitahonjo, Harima-cho, Kako-gun, Hyogo-ken; Hidetoshi Kutsuki, 648-3-606 Aza-Otani, Shioya-cho, Tarumi-ku, Kobe-shi, Hyogo-ken; Junzo Hasegawa, 13-4, Takaoka 2-chome, Okubo-cho, Akashi-shi, Hyogo-ken; Satomi Takahashi, 13-13, Shinwadai 1-chome, Tarumi-ku, Kobe-shi, Hyogo-ken, all of Japan

[21] Appl. No.: 369,164

[22] Filed: Jun. 21, 1989

[30] Foreign Application Priority Data

Jun. 22, 1988 [JP] Japan .................................. 63-153718

[51] Int. Cl.⁴ .......................................... C07D 207/12
[52] U.S. Cl. .................................................. 548/541
[58] Field of Search ........................................ 548/541

[56] References Cited

U.S. PATENT DOCUMENTS 3,542,807 11/1970 Lansford et al. ................... 548/541
3,577,415 5/1971 Cale ..................................... 548/541

OTHER PUBLICATIONS

Brown, Herbert C. et al., "Hydroboration, 78, Reinvestigation of the Hydroboration of N-Substituted-3-pyrrolines, Preparation of N-Benzyl-3-pyrrolidinol and (N-Benzyl-3-pyrrolidinyl)boronate of Very High Enantiomeric Purity," *Journal of Organic Chemistry*, vol. 51 (1986) pp. 4296-4298.

Nemia, Margaret M. Bowers et al., "Synthetic Routes to 3-Pyrrolidinol," *Synthetic Communications*, vol. 13 (1983) pp. 1117-1123.

Bhat, Krishna L. et al., "Synthetic Routes to Chiral 3-Pyrrolidinols," *Synthetic Communications*, vol. 15 (1985) pp. 587-598.

Hashimoto, Mitsunori et al., "A Novel Decarboxylation of α-Amino Acids, A Facile Method of Decarboxylation by the Use of 2-Cyclohexene-1-One as a Catalyst," *Chemistry Letters*, (1986) pp. 893-896.

Binon, F. et al., "Contribution a l'Etude de Dérivés de la Carnitine et de la Bétaine Crotonique," *Bull. Soc. Chim. Belg.*, vol. 72 (1963) pp. 166-177.

Kurtz, Peter et al., "Über 1-Cyan-alkene-(2)," *Liebig Annalen*, vol. 631 (1960) pp. 21-57.

*Primary Examiner*—David B. Springer
*Attorney, Agent, or Firm*—Armstrong, Nikaido, Marmelstein, Kubovcik & Murray

[57] ABSTRACT

A process for preparing 3-pyrrolidinol having the formula (II):

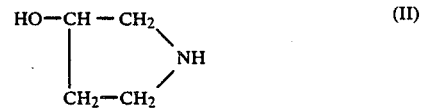

or a salt thereof, which comprises reducing 4-chloro-3-hydroxybutyronitrile having the formula (I):

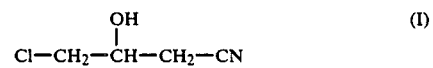

to convert said 4-chloro-3-hydroxybutyronitrile (I) into said 3-pyrrolidinol (II). According to the present invention, 3-pyrrolidinol, particularly optically active 3-pyrrolidinol can be prepared economically and efficiently.

10 Claims, No Drawings

PROCESS FOR PREPARING 3-PYRROLIDINOL

BACKGROUND OF THE INVENTION

The present invention relates to a process for preparing 3-pyrrolidinol or a salt thereof, and more particularly relates to a process for preparing 3-pyrrolidinol or a salt thereof efficiently and economically. 3-Pyrrolidinol is important as an intermediate for preparing calcium blockers, β-lactam antibiotics, and the like.

Hitherto, as processes for preparing 3-pyrrolidinol derivatives, there have been known the following processes:

(1) a process in which an N-substituted 3-pyrroline having the formula (III) is hydroxylated according to hydroboration to produce a compound having the formula (IV) [Journal of Organic Chemistry, 51, 4296(1986) or Synthetic Communications, 13, 1117(1983)],

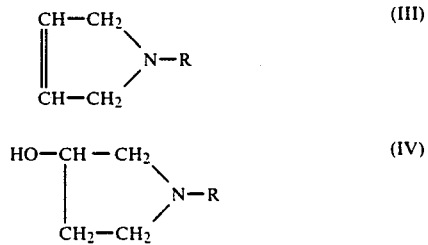

wherein R is a substituent (2) a process in which 1-benzyl malic acid imide having the formula (VI) is prepared from malic acid having the formula (V) as a starting material, and the obtained 1-benzyl malic acid imide (VI) is reduced to give 1-benzyl-3-pyrrolidinol having the formula (VII) [Japanese Unexamined Patent Publication No. 63652/1986 or Synthetic Communications, 15, 587(1985)],

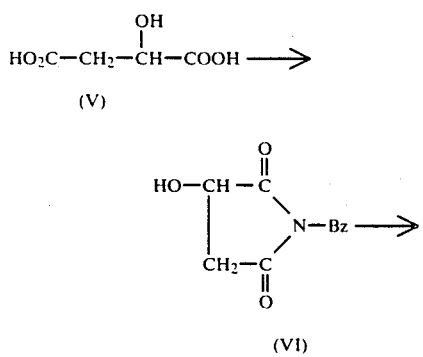

(3) a process in which hydroxyproline having the formula (VIII) is decarboxylated to produce 3-pyrrolidinol (II) [Chemistry Letters, 893(1986)],

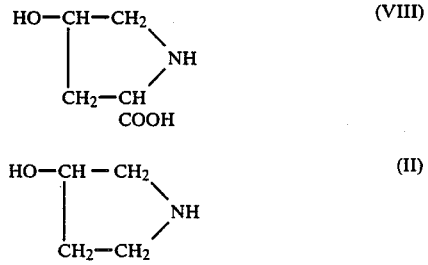

and the like.

However, in the process (1) wherein hydroboration is conducted, and in the process (2) wherein malic acid is used as the starting material, it is necessary to use relatively expensive reagents such as diborane and lithum aluminum hydride. In addition, the process (2) has a disadvantage such that even if optically active malic acid is used as a starting material, racemization occurs partly in a stage of cyclization, consequently, optical resolution must be conducted lastly in order to obtain optically pure 3-pyrrolidinol. Also, the process (3) wherein decarboxylation of hydroxyprolin is conducted has a defect such that hydroxyprolin itself is expensive. Accordingly, all of the processes (1) to (3) are unsatisfactory as the process for practically preparing racemic 3-pyrrolidinol as well as optically active 3-pyrrolidinol.

An object of the present invention is to provide an industrial preparation process of 3-pyrrolidinol, particularly optically active 3-pyrrolidinol, which is economical, simple, easy and efficient.

This and other objects of the present invention will become apparent from the description hereinafter.

SUMMARY OF THE INVENTION

It has now been found that 3-pyrrolidinol can be prepared by reducing 4-chloro-3-hydroxybutyronitrile which can be easily prepared according to a known process in the form of both a racemic 4-chlro-3-hydroxybutyronitrile, and an optically active 4-chloro-3-hydroxybutyronitrile, and that as the above reduction method, catalytic reduction, which is industrially advantageous, can be conducted. Further, it has now been found that when optically active 4-chloro-3-hydroxybutyronitrile is used as a substrate, optically active 3-pyrrolidinol can be prepared.

That is, in accordance with the present invention, there is provided a process for preparing a 3-pyrroldinol having the formula (II):

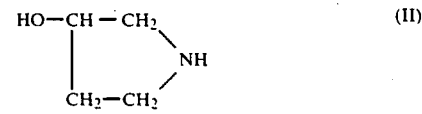

or a salt thereof, which comprises reducing a 4-chloro-3-hydroxybutyronitrile having the formula (I):

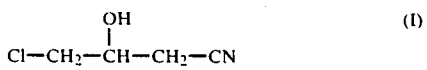

to convert the 4-chloro-3-hydroxybutyronitrile (I) into the 3-pyrrolidinol having the formula (II).

DETAILED DESCRIPTION

4-Chloro-3-hydroxybutyronitrile (I) used in the present invention as the starting material can be prepared according to various known processes. For example, it can be easily prepared by reacting epichlorohydrin (IX) with a cyanating agent such as acetone cyanohydrin, hydrogen cyanide (HCN) or potassium cyanide (KC)), as mentioned below [Bulletin des Societes Chimiques Belgss (Bull. Soc. Chim. Belges) 72, 166(1963); Liebig Annalen (Ann.) 631, 21(1960); or Ger. Offen. DE 938536].

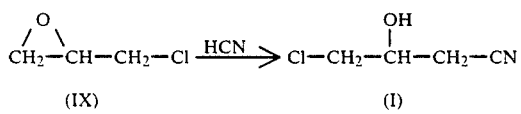

As a process for preparing an optically active, i.e., (R)- or (S)-4-chloro-3-hydroxybutyronitrile, Japanese Unexamined Patent Publication No. 212356/1987 discusses that racemic 2-acetoxy-3-chloropropyl-p-toluenesulfonate (X) prepared from a racemic epichlorohydrin is asymmetrically hydrolyzed with lipase to isolate (R)-2-acetoxy-3-cloropropyl-p-toluenesulfonate (X) and it is reacted with potassium cyanide, KCN in methanol to convert into a (R)-4-chloro-3-hydroxybutyronitrile having the formula (I'), as mentioned below:

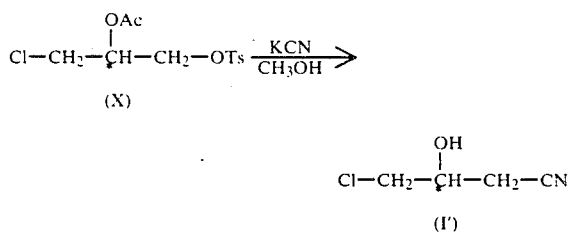

wherein an asterisk (*) represents (R)-configuration with respect to the asymmetric carbon atom.

In the catalytic reduction of the 4-chloro-3-hydroxybutyronitrile (I), any known reducing catalysts can be used so long as they can convert cyano group into a primary amine. Particularly, metal catalysts such as a Raney metal or its alloy, a palladium catalyst, and a platinum catalyst are preferably used. Examples of the catalyts are, for instance, Raney nickel (Raney Ni), platinum oxide ($PtO_2$), rhodium/alumina ($Rh/Al_2O_3$), palladium carbon (Pd(C)), Raney cobalt (Raney Co), Raney nickel-chrome (Raney Ni-Cr), nickel borate ($Ni_2B$), and the like. The catalysts may be used alone or as an admixture thereof.

As a solvent used in the catalytic reduction, solvents usually used in catalytic reduction can be used. Examples of the solvents are, for instance, methanol, ethanol, n-propanol, iso-propanol, butanol, water, acetic acid, dioxane, cyclohexane, hexane, toluene, and the like. The solvents may be used alone or as an admixture thereof.

In the catalytic reduction, due to the catalyst used, reduction temperature, reduction time and basicity of the reduction system, two kinds of the resulting mixture are obtained. That is, there are a case that a mixture mainly containing a primary amine, which is the reduction product of the compound (I) but is noncyclized, is obtained, and a case that a mixture mainly containing 3-pyrrolidinol (II) which is cyclized is obtained. In the later case, cyclization proceeds at the same time as reduction to give the cyclized 3-pyrrolidinol (II) directly. In order to complete the cyclization, it is preferable to conduct the cyclization by further stirring the reduction product under a basic condition. Of course, non-cyclized reduction product as obtained in the former case can be cyclized under the basic condition after the reduction is completed. Generally, there is a tendency that it is easy to obtain the non-cyclized products at room temperature, and when the reduction temperature is elevated to not less than 50° C., there is a tendency that a reduction mixture containing mostly the cyclized product can be obtained. Also, the reduction time becomes longer, there is a tendency that it is easy to cause the cyclization.

The reduction of 4-chloro-3-hydroxybutyronitrile (I) can be conducted as follows:

When using Raney Ni as the catalyst, 4-chloro-3-hydroxybutyronitrile (I) is stirred in methanol in the presence of a catalytic amount (usually from 5 to 20 % by weight) of Raney Ni under a hydrogen pressure of 0.5 to 50 $kg/cm^2$, preferably 1 to 10 $kg/cm^2$, at a temperature of 15° to 150° C, preferably 30° to 80° C, for 1 to 50 hours, preferably 3 to 20 hours to reduce. In such a case, there is a tendency to obtain a reduction mixture containing mainly 3-pyrrolidinol (II). Also, when using Raney cobalt as the catalyst, 4-chloro-3-hydroxybutyronitrile (I) is stirred in methanol in the presence of a catalytic amount (usually from 5 to 20 % by weight) of Raney Co under a hydrogen pressure of 0.5 to 35 $kg/cm^2$, preferably from 1 to 10 $kg/cm^2$, at a temperature of 15° to 150° C, preferably from 30° to 100° C, for 30 minutes to 30 hours, preferably from 1 to 20 hours to reduce. In such a case, the obtained reduction mixture contains mainly 3-pyrrolidinol (II). When using $PtO_2$, Pd(C), $Rh/Al_2O_3$ as the catalyst, the reduction can be conducted under the same conditions as in the case using Raney Co as the catalyst.

When the optically active 4-chloro-3-hydroxybutyronitrile is reduced, the optically active 3-pyrrolidinol can be obtained, that is, (R)-3-pyrrolidinol can be obtained from (R)-4-chloro-3-hydroxybutyronitrile and (S)-3-pyrrolidinol can be obtained from (S)-4-chloro-3-hydroxybutyronitrile without causing racemization.

The reduction product can be isolated by carrying out usual post-treatments, for example, by filtering off the catalyst from the product, then distilling.

The reduction and isolation procedures are not limited to the above-mentioned, and any usual catalytic reduction procedures and isolation procedures can be applied in the invention.

Examples of salts of the 3-pyrrolidinol (II) are, for instance, hydrochloric acid salt, sulphuric acid salt, acetic acid salt, formic acid salt, propionic acid salt, butyric acid salt, phosphoric acid salt, and the like.

According to the present invention, 3-pyrrolidinol (II), particularly optically active 3-pyrrolidinol, can be prepared economically and efficiently from 4-chloro-3-hydroxybutyronitrile (I) which can be easily prepared according to the known processes.

The present invention is more specifically described and explained by means of the following Examples in which all % are by weight unless otherwise noted. It is to be understood that the present invention is not limited to the Examples, and may be made various changes and modifications without departing from the scope or spirit of the present invention.

REFERENCE EXAMPLE 1

[Preparation of 4-chloro-3-hydroxybutyronitrile]

To a solution of 69.5 g of epichlorohydrin and 70.5 g of acetone cyanhydrin in 37.5 ml of acetone was added 1 ml of triethylamine. After the mixture was refluxed with heating for 12 hours, the resulting mixture was distilled uner reduced pressure (2 mmHg) at a temperature of 100° to 106° C. to give 39 g of 4-chloro-3-hydroxybutyronitrile.

$^1$H-nuclear magnetic resonance ($^1$H-NMR) (CDCl$_3$): δ 2.80 (d, 2H, J=5Hz), 3.2 to 3.67 (m, 1H), 3.65 (d, 2H, J=6Hz), 4.1 to 4.22 (m, 1H)

Infrared absorption (IR) spectrum (cm$^{-1}$): (neat) 3420, 2250, 1420, 1310, 1100, 760

REFERENCE EXAMPLE 2

[Preparation of (R)-4-chloro-3-hydroxybutyronitrile]

There were dissolved 10.0 g of (R)-3-chloro-2-acetoxypropyl-p-toluenesulfonate and 2.55 g of potassium cyanide (KCN) in 70 ml of methanol, add the mixture was stirred at 20° C for 19 hours. Potassium toluenesulfonate was filtered off from the reaction mixture and the filtrate was distilled at 115° to 117° C under a pressure of 4 mmHg to give 3.35 g of (R)-4-chloro-3-hydroxybutyronitrile.

$[\alpha]_D^{25} = 17.4$ (C=1, methanol)

EXAMPLE 1

There was dissolved 4 g of 4-chloro-3-hydroxybutyronitrile obtained in Reference Example 1 in 80 ml of methanol, and 500 mg of Raney Ni (W$_7$) was added to the methanol solution. The mixture was stirred under a hydrogen pressure of 5 kg/cm$^2$ at room temperature for 19 hours. After the reduction was completed, the catalyst was filtered off and methanol was distilled away to give a crude 3-pyrrolidinol hydrochloride. To the crude product were added 10 ml of methanol and 1.34 g of sodium hydroxide (NaOH) and the mixture was stirred at room temperature for 30 minutes. Precipitated sodium chloride was filtered off, methanol was distilled away, and then distillation was carried out under reduced pressure (3 mmHg) at 100° to 120° C to give 2.12 g of 3-pyrrolidinol.

$^1$H-NMR(CDCl$_3$): δ 1.56 to 2.17 (m, 2H), 2.63 to 3.3 (m, 4H), 3.8 (bs, 1H), 4.23 to 4.47 (m, 1H)

IR spectrum (cm$^{-1}$): (neat) 3320, 2960, 2900, 1450, 1350, 1075, 990, 900

EXAMPLE 2

The procedure of Example 1 was repeated except that 4 g of (R)-4-chloro-3-hydroxybutyronitrile obtained in Reference Example 2 was used to give 2.23 g of (R)-3-pyrrolidinol.

Hydrogen chloride gas was blown into an isopropanol solution of (R)-3-pyrrolidinol to give (R)-3-pyrrolidinol hydrochloride, and it was isolated according to a usual manner. As to the obtained product, $[\alpha]_D^{20}$ was measured. The results are shown as below:

| Found value | Known value |
|---|---|
| $[\alpha]_D^{20} = 7.6$ (C = 3.8, methanol) | $[\alpha]_D^{20} = 7.6$ (C = 3.45, methanol) described in Chemistry letters |
| | 895(1986) |

EXAMPLE 3

There was dissolved 4 g of 4-chloro-3-hydroybutyronitrile obtained in Reference Example 1 in 80 ml of methanol, and 50 mg of platinum oxide, PtO$_2$ was added to the solution. The mixture was stirred under a hydrogen pressure of 5 kg/cm$^2$ at room temperature for 15 hours. After completing the reduction, the procedure of Example 1 was repeated to give 2.12 g of 3-pyrrolidinol.

EXAMPLE 4

The procedure of Example 3 was repeated except that 50 mg of rhodium/alumina, Rh/Al$_2$O$_3$ was used instead of PtO$_2$ to give 2.05 g of 3-pyrrolidinol.

EXAMPLE 5

There was dissolved 4 g of 4-chloro-3-hydroxybutyronitrile obtained in Reference Example 1 in of methanol, and 500 mg of 5 % palladium carbon Pd(C) and 20 ml of 2N hydrochloric acid were added to the solution. After the mixture was stirred under a hydrogen pressure of 5 kg/cm$^2$ at room temperature for 20 hours, the catalyst was filtered off. After 1.5 g of NaOH was added thereto, the mixture was stirred at room temperature for 22 hours. The solvent was distilled away, ethanol was added to the residue and sodium chloride was filtered off. Ethanol was distilled away, which was distilled to give 1.97 g of 3-pyrrolidinol.

EXAMPLE 6

In 80 ml of methanol was dissolved 4 g of 4-chloro-3-hydroxybutyronitrile obtained in Reference Example 1, and 400 mg of Raney Co was added thereto. The mixture was stirred under a hydrogen pressure of 7 kg/cm$^2$ at 70° C for 10 hours. After completing the reduction, the procedure of Example was repeated to give 2.05 g of 3-pyrrolidinol.

In addition to the ingredients used in the Examples, other ingredients can be used in Examples as set forth in the specification to obtain substantially the same results.

WHAT WE CLAIM IS:

1. A process for preparing 3-pyrrolidinol having the formula (II):

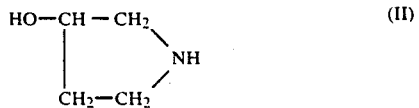

or a salt thereof, which comprises reducing 4-chloro-3-hydroxybutyronitrile having the formula (I):

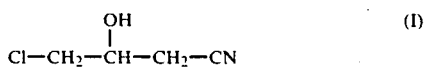

to convert the 4-chloro-3-hydroxybutyronitrile (I) into the 3-pyrrolidinol (II).

2. The process of claim 1, wherein said 4-chloro-3-hydroxybutyronitrile (I) is catalytically reduced in the presence of a metal catalyst.

3. The process of claim 1, wherein said 4-chloro-3-hydroxybutyronitrile (I) is an optically active (R)-form or (S)-form.

4. The process of claim 2, wherein said 4-chloro-3-hydroxybutyronitrile (I) is an optically active (R)-form or (S)-form.

5. The process of claim 1, wherein said metal catalyst is at least one catalyst selected from the group consisting of Raney nickel, platinum oxide, rhodium/alumina and a palladium catalyst.

6. The process of claim 2, wherein said metal catalyst is Raney nickel.

7. The process of claim 2, wherein the cyclization is caused at the same time as the reduction by using a Raney nickel to directly give said compound (II).

8. The process of claim 2, which further comprises cyclizing an uncyclized reduction product of said compound under a basic condition.

9. The process of claim 2, wherein said metal catalyst is a Raney cobalt.

10. The process of claim 2, wherein the cyclization is caused at the same time as the reduction by using a Raney cobalt to directly give said compound (II).

* * * * *

UNITED STATES PATENT AND TRADEMARK OFFICE
CERTIFICATE OF CORRECTION

PATENT NO. : 4,910,320
DATED : March 20, 1990
INVENTOR(S) : INOUE et al

It is certified that error appears in the above-identified patent and that said Letters Patent is hereby corrected as shown below:

On the cover page, after Item [76], the following should appear:

--[73] Assignee: Kanegafuchi Kagaku Kogyo Kabushiki Kaisha, Osaka, Japan--.

Signed and Sealed this

Twenty-fifth Day of June, 1991

Attest:

HARRY F. MANBECK, JR.

*Attesting Officer*     *Commissioner of Patents and Trademarks*